United States Patent [19]

Mesters et al.

[11] Patent Number: 4,657,888
[45] Date of Patent: Apr. 14, 1987

[54] PROCESS FOR THE PRODUCTION OF A CATALYST

[75] Inventors: Carolus M. A. M. Mesters, Utrecht; John W. Geus, Bilthoven; Eugène G. M. Kuijpers, Apeldoorn; Onno L. J. Gijzeman, Utrecht, all of Netherlands

[73] Assignee: VEG-Gasinstituut N.V., Del.X

[21] Appl. No.: 684,621

[22] Filed: Dec. 21, 1984

[30] Foreign Application Priority Data

Dec. 31, 1983 [DE] Fed. Rep. of Germany ....... 3347677

[51] Int. Cl.$^4$ ......................... B01J 23/48; B01J 23/72; B01J 23/76; B01J 23/89
[52] U.S. Cl. .................................. 502/331; 502/326; 502/330; 518/713
[58] Field of Search ............... 502/244, 326, 327, 331, 502/330, 245; 518/713

[56] References Cited

U.S. PATENT DOCUMENTS

| | | | |
|---|---|---|---|
| 1,843,540 | 2/1932 | Casale | 423/655 |
| 2,234,246 | 3/1941 | Groombridge et al. | 252/257 |
| 2,753,367 | 7/1956 | Rottig et al. | 502/331 X |
| 3,371,050 | 2/1968 | Taylor et al. | 252/459 |
| 3,668,148 | 6/1972 | Van Beek et al. | 252/440 |
| 3,668,149 | 6/1972 | Geus et al. | 252/448 |
| 3,840,479 | 10/1974 | Geus | 252/471 |
| 3,850,841 | 11/1974 | Aldridge et al. | 252/373 |
| 3,899,577 | 8/1975 | Sugier | 423/656 |
| 3,962,140 | 6/1976 | Alcorn et al. | 518/713 X |
| 4,113,658 | 9/1978 | Geus | 252/454 |
| 4,124,629 | 11/1978 | Hansford | 260/449.6 M |
| 4,128,730 | 12/1978 | Reich | 568/914 |
| 4,157,315 | 6/1979 | Michels et al. | 252/458 |
| 4,190,560 | 2/1980 | Geus et al. | 252/459 |
| 4,297,245 | 10/1981 | Bartley et al. | 502/326 X |
| 4,459,370 | 7/1984 | van der Wal et al. | 502/338 |
| 4,478,800 | 10/1984 | van der Wal et al. | 423/230 |

FOREIGN PATENT DOCUMENTS

| | | | |
|---|---|---|---|
| 1767202 | 5/1975 | Fed. Rep. of Germany . | |
| 490090 | 8/1938 | United Kingdom | 518/713 |
| 1220105 | 1/1971 | United Kingdom . | |

*Primary Examiner*—W. J. Shine
*Attorney, Agent, or Firm*—Mandeville and Schweitzer

[57] ABSTRACT

A process for the production of a catalyst containing metallic copper, silver, gold, platinum or palladium in finely divided form as basic metal and at least one metal of Group VIII of the Periodic System of Elements as active component on an inert, refractory support, the catalyst containing the basis metal being heated to a temperature above 100° C. and one or more carbonyls of metals different from the basis metal and belonging to Group VIII of the Periodic System of Elements being allowed to act on the heated catalyst so that those metals are alloyed into the basis metal. The invention also refers to catalysts obtained by such process.

19 Claims, No Drawings

PROCESS FOR THE PRODUCTION OF A CATALYST

BACKGROUND OF THE INVENTION

This invention relates to a process for the production of a catalyst which contains on an inert, refractory support metallic copper, silver, gold, platinum or palladium in finely divided form and at least one metal of Group VIII of the Periodic System of Elements as active component.

Catalysts of this type may be produced by precipitating two or more metals in the form of oxidic compounds or other water-insoluble compounds onto the inert, refractory support from a suspension containing the inert support in suspension and the metals to be precipitated in the form of ions. The support thus loaded is separated off, calcined and reduced (U.S. Pat. No. 3,371,050).

A major disadvantage of this process lies in the fact that the active component is initially deposited on the support in the form of oxidic compounds which then have to be reduced. This reduction step is time-consuming and, in some cases, can only be carried out by very rigorous reduction methods if complete reduction to the metal is to be achieved. Another problem which applies in particular to catalysts containing several metals as active component lies in the fact that the oxidic compounds do not form mixed lattices that easily. This causes the formation of an inhomogeneous end product i.e. the alloy particles comprising both metals show considerable variations in composition from one particle to another.

The object of the present invention is readily to produce catalysts of the type mentioned at the beginning, the catalysts obtained containing the active component completely or largely in metallic form. It has surprisingly been found that this object can be achieved if at least one of the active components is deposited as a metal from the corresponding carbonyl, onto a precursor comprising the basis component in metallic form.

SUMMARY OF THE INVENTION

Accordingly, the present invention relates to a process for the production of a catalyst containing metallic copper, silver, gold, platinum or palladium in finely divided form as the basis metal and at least one metal of Group VIII of the Periodic System of Elements as active component on an inert, refractory support, characterised in that the catalyst containing the basis metal is heated to a temperature above 100° C. and one or more carbonyls of metals different from the basis metal and belonging to Group VIII of the Periodic System is allowed to act thereon in order to alloy those metals into the basis metal.

Preferred starting materials are catalysts which contain metallic platinum or palladium or more preferably metallic copper on the support.

According to the invention, therefore, the problem as stated above is solved surprisingly easily by allowing metal carbonyls to act on a basis catalyst containing the basis metal, so that the metals of those carbonyls are alloyed into the basis metal.

In the production of the catalyst according to the invention the temperature of the catalyst containing the basis metal should be below 700° C.

The metal to be alloyed into the basis metal is preferably iron and/or nickel.

It is also preferable for the catalyst used as starting material to contain from 5 to 50% by weight of basis metal, based on the weight of the support and basis metal together.

In the fluidised bed preparation procedure, since the gaseous carbonyls are extremely reactive, they are best present in admixture with non-oxidizing gases, preferably nitrogen, the content of gaseous carbonyls in the gas mixture amounting to at least 0.1% by volume, preferably to between 0.5 and 1.5% by volume and, more preferably, to between 0.6 and 1.1% by volume.

The addition of some hydrogen to the gas offers a possibility to keep the basis catalyst in the reduced form during decomposition of the metal carbonyl over the basis catalyst.

In one variant of the process, the carbonyls are allowed to act on the catalyst used as starting material in a fluidised bed reactor in which the catalyst particles are present in fluidised form.

In another embodiment, it is preferred to thoroughly mix the catalyst containing the basis metal with one or more metal powders of metals different from the basis metal and belonging to Group VIII of the Periodic System and to allow carbon monoxide to act on the resulting mixture so that metal carbonyl is formed in situ, i.e. carbonyls of the metals to be alloyed in are formed. This method is referred to as the stationary method.

DETAILED DESCRIPTION OF THE INVENTION

Where production is carried out in a fluidised bed reactor, the particle size of the basis catalyst is best between 0.05 mm and 1.0 mm. In addition, the catalyst particles best differ from one another as little as possible in particle size so that a satisfactory fluidised bed is obtained and particularly large, heavy particles do not sink to the bottom or particularly small, light particles float to the top. Accordingly, the particle size of the catalyst particles best shows a narrow deviation range, preferably ±20% from that particle size which is common to most of the particles. This is known to the expert on the subject of fluidised bed reactions. To avoid misunderstanding, we point to the fact that in the above paragraph, with particle size is meant the size of the powder particles, not the size of the copper particles adherent to the support particles. Those copper metal particles are much smaller. In many cases both metals are even precipitated separately from one another. It is of course important to ensure that the metal carbonyl does not decompose outside the fluidised bed. Accordingly, the entrance to the reactor should be cooled, best to the temperatures below about 150° C. and preferably to temperatures below about 100° C. This also applies to the screen by which the fluidised bed is closed off underneath. In order to heat the catalyst particles above the screen in the fluidised bed as quickly as possible to the required temperature, it is best to introduce hot inert gases for heating the catalyst particles in a zone above the cooled screen by which the fluidised bed is closed off underneath. In the case of small reactors, the desired temperature gradient may be obtained by external heating and cooling systems.

In the variant in which metal powder is exposed to the action of carbon monoxide in admixture with the basis catalyst used as starting material (i.e. the catalyst containing the basis metal on a support), it can be of advantage alternately to heat the mixture to relatively high temperatures and then to somewhat lower temperatures, for example first to a relatively low temperature of from about 100° C. to 250° C. for a certain period, for example 10 minutes to 2 hours, then to keep it at a higher temperature, best at least 100° C., for a certain period, for example 10 minutes to 2 hours, and then to cool it again, best by at least 100° C., and to repeat this cycle of heating and cooling either once or several times. The nickel particles react with the carbon monoxide at relatively low temperatures until an equilibrium state in regard to the formation of metal carbonyl is estabished in the reactor. At elevated temperature, metal carbonyl is less stable, i.e. decomposes, preferably at the surface of the basis metal. In this way, the metal to be alloyed in is incorporated into the basis metal. If cooling and heating are then applied again, this mechanism is repeated until the desired content of metal to be incorporated is reached in the basis metal, i.e. until essentially all the powder-form metal added has been alloyed into the basis metal.

In the fluidised bed process, the catalyst should best have a temperature above 200° C. and preferably above 300° C. in the fluidised bed. In a special procedure according to the invention, hot, non-oxidizing gases are best introduced into the fluidised bed reactor for the purpose of heating the catalyst particles to the desired temperature in a zone above the screen by which the fluidised bed is closed off underneath and which screen is kept at a temperature preferably below 150° C.

If the catalyst is produced by passing carbon monoxide over a mixture of the basis catalyst and metal powder, more than 90% by weight of the metal powder best consists of monocrystalline metal particles without grain boundaries.

If the catalyst is produced by the stationary method, the basis catalyst may be present in the form of pellets or other compact bodies.

If, in the stationary method, the metal powder is not present in monocrystalline form, so that crystal boundaries are present between the individual crystallites, it is important that all such metal powder should be consumed during production of the catalyst and does not remain behind in the catalyst as metal powder. This is because it could give rise to the formation of carbon deposits if the catalyst is used at a later stage. If, however, metal powder present solely in monocrystalline form with no crystal boundaries is used in the production of the catalyst, it is not absolutely necessary for all the metal powder to be consumed by reaction with carbon monoxide, since this metal powder has a much decreased tendency for such carbon formation.

The inert, refractory supports used may be any of the substances having a large specific surface which are commonly used in the catalyst field. Examples of those substances are aluminium oxide, silicon dioxide-aluminium oxide, silicon dioxide-magnesium oxide, zirconium dioxide, silicon dioxide-zirconium dioxide, titanium dioxide, silicon dioxide-zirconium dioxide-titanium dioxide, crystalline or amorphous aluminosilicate molecular sieves and metal phosphates.

It is preferred to use a silicon dioxide support having a specific surface of more than 50 m$^2$/g. It is possible to use the commercially available products based on kieselguhr, i.e. natural products, or synthetically produced, finely divided silicon dioxide, for example of the type, commercially available as Aerosil ®. If kieselguhr is used, it should have a specific surface of from about 5 to 40 m$^2$/g. In the production of the catalyst, however, the particles break up and a much larger surface of from about 60 to 150 m$^2$/g is obtained.

The upper limit to the quantity of basis metal which is bound to the support depends essentially on the presence of a sufficient quantity of basis metal and metal to be alloyed in with a suffiently large specific surface. In general, the upper limit amounts to about 50% by weight of metallic basis metal, based on the total weight of the catalyst after its production, when the basis metal is copper. When the basis metal is palladium or platinum, the upper limit should amount to 10% by weight and preferably to 5% by weight, based on the total weight of the catalyst. The treatment with carbonyls is preferably continued until at least 1% by weight of the metals of Group VIII of the Periodic System, based on the total weight of the catalyst, has been alloyed into the basis metal. The upper limit to the content of metal alloyed in preferably amounts to 10% by weight and, more preferably, to 5% by weight, based on the total weight of the metals.

Accordingly, the catalyst produced in accordance with the invention is distinguished by the fact that the metals of Group VIII of the Periodic System (other than the basis metal) are alloyed into the matrix of the basis metal. Preferably at least 90% by weight and, more preferably, at least 95% by weight of all the metal of Group VIII of the Periodic System present in the catalyst, that metal being different from the basis metal, are incorporated in the basis metal so uniformly that the particles of basis metal and metal to be alloyed in contain at most 30% by weight of metal to be alloyed in, based on the total weight of basis metal and metal to be alloyed in. The methods described herein are also suitable for the incorporation of other Group VIII metals in accordance with the invention.

The specific surface of the metallic particles of basis metal and incorporated metal of Group VIII of the Periodic System which are bound to the support best amounts to at least 20 and preferably to at least 40 m$^2$/g of those metallic particles and best to at most 80 m$^2$/g. A specific surface as large as this of those metal particles is obtained in accordance with the invention, although to that end the basis catalyst must of course contain the basis metal in correspondingly fine distribution, i.e. with a correspondingly large surface. The terms "carrier" and "support" are equivalent.

The invention provides also a method to produce novel metal alloy catalysts on a refractory support material, with unexpected properties in catalysing a number of chemical reactions.

Catalysts that can be produced according to the invention are for instance:
Ni-Cu alloy on a refractory support,
Fe-Cu alloy on a refractory support,
Ni-Fe-Cu alloy on a refractory support.

Due to their special structure, these catalyst have superior properties over other known catalysts, even over "alloy-type" catalysts.

This is caused by two phenomena:

1. The alloy particles bound to the support show little variation in composition from one particle to another.

2. The secondary (or "tertiary" etc.) metal is present in a relatively low concentration in the particle on a volume (or weight) basis, but it concentrates at the surface of the basis metal and therefore causes a relatively high catalytic activity.

(This is shown with infrared absorption measurements as herein described).

Metals which can be alloyed into the basis metal are nickel and iron, and the catalysts thus produced can be used very favourably in a number of chemical conversions involving hydrocarbons and/or carbonmonoxide. Known supported "pure" nickel or iron metal catalysts tend to cause carbon deposition at temperatures where they should be operated, leading to catalyst deactivation and possibly reactor plugging. This tendency for carbon formation is very substantially suppressed with catalysts of the invention, probably due to the fact that the basis metal, in particular copper, shows only a very small tendency for causing carbon deposition. The secondary metal is "embedded" in the copper matrix and can cause no carbon deposition in this configuration, probably due to the specific mechanism of carbon formation. Catalysts of the invention can therefore be used very favourably in e.g. the following reactions:

| Catalyst | Reaction |
|---|---|
| Ci-Ni on support | methanation |
| | shift-methanation |
| | Low-temperature reforming of hydrocarbons |
| Cu-Fe on support | Fischer-Tropsch reaction with controllable specificity |
| Cu-Fe—Ni on support | Fischer-Tropsch reaction |

In the methanation reaction, carbon monoxide reacts with hydrogen to form methane according to:

$$CO + 3H_2 \rightarrow CH_4 + H_2O.$$

In the shift-methanation reaction, carbon monoxide reacts with hydrogen or steam according to either one or a combination of both following reactions:

$$2CO + 2H_2 \rightarrow CH_4 + CO_2$$

$$4CO + 2H_2O \rightarrow CH_4 + 3CO_2$$

In the low-temperature reforming of hydrocarbons they react with steam to form a product gas predominatly containing methane, and also carbon dioxide and hydrogen and only a small amount of carbon monoxide. Processes aimed at these conversions are operated at pressures of 0.2 to 2.5 MPa and temperatures between about 300° and 600° C. In the Fisher-Tropsch reaction carbon monoxide reacts with hydrogen to form a mixture of hydrocarbons, comprising both alkanes and alkenes with a carbon number essentially below 10, and lower alcohols according to the following reactions:

$$nCO + 2nH_2 \rightarrow C_nH_{2n} + nH_2O \quad (n = 2, 3 \ldots) \quad (1)$$

$$mCO + (2m+1)H_2 \rightarrow C_mH_{2m+2} + mH_2O \quad (M = 1, 2, 3, \ldots) \quad (2)$$

$$pCO + 2pH_2 \rightarrow C_{p-1}H_{2p-1}CH_2OH + (p-1)H_2O \quad (p = 1, 2, 3 \ldots) \quad (3)$$

One feature common to all the above reactions is that carbon monoxide and/or hydrocarbons are present in the gas phase on the catalyst as starting products or as reaction products, possibly even on an intermediate basis. These reactions are carried out in known manner, however using the catalyst according to the invention.

Particularly high activity with very little risk of carbon deposition was observed in the case of the above-mentioned methanation reaction. In this case, the entry temperature for the methanation reactor can be kept very low, for example in the range from about 250° to 350° C. Since considerable quantities of nickel carbonyl are formed in state-of-the-art processes, the exit temperatures of the methanation reactor have to be kept so high that the nickel carbonyl is redissociated at the temperatures in question and, hence, is unable to pass into the waste gas steam, which must be strictly avoided (inter alia on account of the high toxicity level). According to the invention, the exit temperatures can be kept lower, for example below about 550° C. and preferably below 500° C.

The presence of monometallic nickel particles in the catalyst can be detected by magnetic methods. It is known that, at temperatures above 60° K., copper-nickel alloys containing less than 30 atom % of nickel are diamagnetic (cf. H. C. van Elst et al., Physica 20 (1962) 1297). As a result, if all the nickel present is alloyed with copper, only very weak magnetisation, which is not dependent on temperature, is measured, even in a strong magnetic field of, for example, $10^4$Oe. If, however, a significant quantity of the nickel in the catalyst present in the form of monometallic crystallites, these particles show superparamagnetism (cf. Selwood in "Chemisorption and Magnetization") or even ferromagnetism. The presence of ferromagnetic particles produces a steep increase in magnetisation for a given strength of the magnetic field. The magnetisation of superparamagnetic particles is temperature-dependent. Nickel-copper alloys with a nickel content of from 30 to 50 atom % show weak paramagnetism which, compared with monometallic nickel particles, gives rise to only weak magnetisation. 30 atom % of nickel in the nickel-copper alloy corresponds to about 28% by weight of nickel. The paramagnetic moment of the reduced catalyst is no higher than 1.0 $\mu m_b$ per nickel atom and/or nickel ion.

The infrared absorption spectra of CO irreversibly adsorbed on Ci-Ni-alloy catalysts show only one wide adsorption band at around 2000 cm$^{-1}$. It is known that CO adsorbed on pure copper catalysts is readily desorbed, whereas CO adsorbed on pure nickel catalysts cannot be desorbed by evacuation at room temperature. Accordingly, the absorption band observed after evacuation must be attributed at "Ni-like" places.

On pure Ni-catalysts, irreversibly adsorbed CO gives rise to two adsorption bands, the band with a maximum at 2045 cm$^{-1}$ being attributed to linearly bound CO and the other band with a maximum at 1950 cm$^{-1}$ being attributed to bridge-bound CO. J. A. Dalmon, M. Primet, G. A. Martin and B. Imelik, Surface Sci., 50 (1975) 95 observed that the maxima of both bands were shifted to lower frequencies when a nickel-on-silica gel catalyst was alloyed with copper. In addition to the frequency shift, they also observed a reduction in the adsorption intensity of both bands with increasing copper content. The band assigned to bridge-bound CO showed a very much greater reduction than the band assigned to linearly bound CO. This was explained by the fact that a larger number of nickel atoms per binding place is required for bridge-bound CO than for linearly bound CO. In fact, the adsorption band of bridge-bound CO disappears completely at copper contents above 50%.

The frequency shift is necessarily indicative of the fact that, after exposure to a CO-atmosphere, our completely reduced copper-nickel catalysts show a surface composition in which nickel is present as an isolated dilute species in a copper matrix.

In addition to the above mentioned features we have found that our catalysts of the invention can be used very favourably in many chemical conversions when a basis catalyst with a very homogeneous distribution of small copper particles is used, leading to an evenly homogeneously distributed catalyst of the invention with very small alloy particles on the support material.

Accordingly, the present invention relates to a copper-nickel catalyst containing on an inert, refractory carrier metallic copper and nickel as active component bound to the carrier, characterised in that (a) the catalyst contains at least 5% by weight, based on the total weight of the catalyst, of metallic copper, (b) the catalyst contains less than 25% by weight of metallic nickel, based on the total weight of metallic copper and metallic nickel, the catalyst containing at least 1% by weight of metallic nickel, based on the total weight of the catalyst, (c) at least 80% by weight of the nickel is alloyed in the metallic copper, (d) the copper-nickel alloy is present on the carrier in small metal particles with an average particle size of less than 14 nm.

Furthermore, the present invention relates to a copper-iron catalyst containing on an inert, refractory carrier metallic copper and iron as active component bound to the carrier, characterised in that (a) the catalyst contains at least 5% by weight, based on the total weight of the catalyst, of metallic copper, (b) the catalyst contains less than 25% by weight of metallic iron, based on the total weight of metallic copper and metallic iron, the catalyst containing at least 1% by weight of metallic iron, based on the total weight of the catalyst, (c) at least 80% by weight of the iron is alloyed in the metallic copper, (d) the copper and iron are present on the carrier in small metal particles with an average particle size of less than 14 nm.

Furthermore, the present invention relates to a copper-nickel-iron catalyst containing on an inert, refractory carrier metallic copper and nickel and iron as active component bound to the carrier, characterised in that (a) the catalyst contains at least 5% by weight, based on the total weight of the catalyst, of metallic copper, (b) the catalyst contains less than 25% by weight of metallic nickel and iron, based on the total weight of metallic copper and metallic nickel and iron, the catalyst containing at least 1% by weight of metallic nickel and iron, based on the total weight of the catalyst, (c) at least 80% by weight of the nickel and iron are alloyed in the metallic copper, (d) the copper-nickel-iron alloy present on the carrier in small metal particles with an average particle size of less than 14 nm.

It is preferred, that the weight ratio between copper on one side, and nickel and/or iron on the other side in the catalyst is between 16 and 100. This means, that the catalyst contains on one part by nickel or iron or both between 16 and 100 parts by weight copper. It is furthermore preferred, that the catalyst contains less than 13% by weight, more preferred less than 10% by weight and most preferably less than 6% by weight of metallic nickel or iron or both, based on the total weight of metallic copper and metallic nickel or iron or both.

In case of catalysts containing nickel and iron the range between them can vary widely, depending on the intended use of the catalyst. In order to obtain an activity remarkably different from the activity of a catalyst containing only nickel or iron in some cases already on amount of 2% by weight of iron, based on the weight of the nickel, is effective. Preferably the amount of iron should be at least 5%, most preferably at least 10%. The same applies for the content of nickel in a catalyst, which contains as the major component iron.

An essential feature of the catalyst according to the invention is that as large a percentage as possible of the nickel and/or iron in the catalyst is present in the form of metallic nickel and/or iron in the matrix of metallic copper. Preferably, at least 90% by weight and, more preferably, at least 95% by weight and most preferably at least 98% by weight of the nickel and/or iron in the catalyst is alloyed in the metallic copper.

As pointed out above already it is an essential feature that the metal particles consisting of the copper-nickel and/or iron alloy have a very small particle size, and it is preferred that the average particle size of the metal particles is less than 12 nm, more preferably less than 10 nm and most preferably less than 8 nm.

Another preferred feature of the invention is, that the nickel and/or iron alloyed in the metallic copper are distributed so homogeneously, that they are present in alloy particles containing at most 30% by weight of metallic nickel and/or iron, based on the total weight of the metals.

EXAMPLE 1

The starting material is a copper-silicon dioxide catalyst produced in known manner by homogeneously forming hydroxyl ions in a suspension of the finely divided silicon dioxide of large specific surface, which is used as the support material, in an aqueous solution of a copper salt by the decomposition of dissolved urea at around 90° C. and thus depositing copper in the form of oxidic compounds on the support (cf. DE-PS No. 17 67 202). The silicon dioxide used is a commercially available product (Aerosil ®) having a specific surface of 200 m²/g. The loaded support, which contains approximately 30% by weight of metallic copper, based on the total weight of the loaded support, was dried for 20 hours at 110° C., ground and sieved. The fractions having particle sizes of from 0.2 to 0.7 mm ±0.05 mm were used for further processing. The subsequent reaction was carried out in a fluidised bed reactor.

The catalyst, which is present in fluidised form, was calcined by passing over a mixture of 10% by volume of oxygen and 90% by volume of nitrogen at 400° C. The catalyst was then reduced by passing a mixture of 10% by volume of hydrogen and 90% by volume of nitrogen through the fluidised bed reactor for at least 5 hours at 430° C. The nitrogen is used to ensure that a sufficiently vigorous gas stream keeps the catalyst in the fluidised state.

In a small stainless steel reactor having a holding capacity of 50 ml, nickel carbonyl was produced by treating nickelpellets, which had been reduced for 48 hours at 450° C. in an atmosphere of equal parts by volume of hydrogen and argon, with carbon monoxide at a temperature of 70° C. and under a pressure of 0.3 MPa.

The resulting mixture of nickel carbonyl and carbon monoxide was introduced into a gas mixing chamber in a quantity of 50 ml/minute together with a gas stream of hydrogen (5%), argon (5%) and nitrogen (90%) in a quantity of ±4 liters per minutes. The hydrogen was used to prevent oxidation of the reduced metal particles by oxygen impurities possible present in the large quantity of nitrogen used. The gas stream leaving the gas mixing chamber was introduced into the fluidised bed reactor which contains the copper catalyst in fluidised form. The temperature of the catalyst in the fluidised bed reactor during decomposition of the nickel carbonyl amounted to 300°-350° C. At that temperature, the nickel carbonyl dissociates completely on copper monocrystals. To prevent the nickel carbonyl $Ni(CO)_4$ from decomposing before reaching the catalyst under the effect of excessive temperatures below or inside the (glass) filter which forms the lower boundary of the fluidised bed, only the upper part of the reactor above that (glass) filter was heated. The lower part was cooled by an air stream. As a result, the nickel was only deposited above the filter, no visible deposition of nickel taking place in the lower part. Samples of the catalyst were removed from the reactor at various time intervals and analysed. The nickel content was determined by atomic absorption spectroscopy (AAS). Analysis was carried out by dissolving a certain quantity of the catalyst in a mixture of nitric acid and hydrochloric acid in which the active metals dissolve completely in contrast to the silicon dioxide. The silicon dioxide particles were centrifuged off from the solution and washed because these solid particles would interfere with the AAS measurement. The amount of nickel in the acid solution was measured at a wavelenght of 352.4 nm in an acetylene-air flame. The large quantities of copper presented no problem in that respect.

The characteristic data of a bimetallic catalyst thus obtained are shown in the following table:
Copper content (completely reduced catalyst): 29.1% by weight
Nickel content: 4.0% by weight
BET-surface: 450 m²/g
specific metal surface:
 per gram of catalyst: 19 m²
 per gram of metallic copper and nickel: 64 m²
 mean particle size: 11 nm
(The figures quoted above are averages of values determined by various methods, namely: electron miscroscopic, X-ray line widening and degree of chemisorption).

Less than 1% by weight of the total weight of the nickel is not alloyed in copper particles.

EXAMPLE 2

20 g of a catalyst, which contains 30% by weight of metallic copper, based on the total weight of the catalyst, on finely divided silicon dioxide as support (Aerosil ®), were thoroughly mixed with 1 g of a very fine nickel powder (particle size 0.1 μm) and the resulting mixture tabletted. The nickel powder had been obtained from nickel carbonyl and was largely present in the form of monicrystalline nickel crystals. The mixture of catalyst and nickel powder was reduced for 6 hours at 430° C. in a gas stream containing 10% by volume of hydrogen and 90% by volume of nitrogen. The mixture was then cooled to 110° C. and subsequently exposed for about 1 hour to a static CO-atmosphere under a pressure of about 0.1 MPa. After this treatment, the temperature in the reactor was increased to 450° C. at a rate of 6° C. per minute and then kept at that level for 15 minutes. The mixture was then cooled to 110° C. This process of increasing and lowering the temperature was repeated twice. After the third increase in temperature, a sample was removed from the reactor and analysed avoiding oxidation of the catalyst.

As much of the nickel powder as possible was magnetically removed. The remaining catalyst was analysed by infrared spectroscopy of absorbed carbon monoxide. The presence of pure nickel is indicated by the band at 2045 $cm^{-1}$. However, a band was also observed at 2005 $cm^{-1}$, indicating that approximately 5% by weight of nickel, based on the total weight of nickel and copper, were present in the catalyst in the form of an alloy with copper. (Measuring techniques are described in Surface Science 50 (1975), 95–108).

EXAMPLE 3

As a precursor for the preparation of an iron-copper alloy on silica catalyst, a copper on silica catalyst as mentioned in example 1 was prepared. A sieve fraction of 0.4 to 0.8 mm was used (average deviation ±0.05). 8 g of this catalyst was brought into fluidisation in a pure nitrogen stream and calcined at 400° C. for 16 hours. The sample was subsequently reduced for 16 hours at 400° C. in an atmosphere of 50% hydrogen (by volume) in argon. The reduction was done with a lower space velocity in non-fluidised conditions at a space velocity of about 800 $h^{-1}$.

Iron carbonyl was prepared in a-stainless steel reactor by treating iron pellets that were previously reduced for 64 hours at 400° C. in 10 volume % hydrogen in argon atmosphere, in a carbon monoxide atmosphere at room temperature and a pressure of 0.4 MPa.

The ironpentacarbonyl prepared in this way is present in the preparation room in liquid form.

A mixture of the ironpentacarbonyl and carbonmonoxide was led into a mixing chamber at a rate of 50 ml/min., together with a gas stream containing 5 volume % hydrogen, 5 volume % argon and balance nitrogen. This mixture was then led to the reactor at a flow of 4 l/min. The reactor, containing the copper on silica catalyst in fluidised condition, was kept at 350° C., at which temperature the ironpentacarbonyl decomposed onto the copper, forming an iron-copper alloy on silica catalyst with very small active alloy particles.

After certain time periods, samples were taken from the reactor in order to determine iron content in the copper by using Atomic Absorption Spectroscopy.

A suitable catalyst prepared in this way was characterised by the following properties:
30.5 weight % copper
6.1 weight % iron
63.4 weight % silica
Average particle size 11 nm.
Then it was determined whether the iron and copper had indeed formed an alloy by use of infrared spectroscopy.

The catalyst was cooled down and then passivated statically in air. Then an infrared transparent tablet was pressed and placed in a cell with a vacuum and gas-dosage system. After a reduction treatment for 16 hours at 450° C. and evacuating 2 hours at 410° C. the sample was cooled down. Then 100 torr carbonmonoxide was dosed at ambient temperature. In the infrared spectre two peeks are observed that can be attributed to CO-Cu (2135 $cm^{-1}$) and CO-Fe (2024 $cm^{-1}$) absorption. This latter band very gradually shows an intensity increase over time. This is caused by the slow migration of iron in the copper matrix to the surface of the copper particles. After evacuation only this later band was still observed in the spectre.

This clearly shows that 1. an alloy has been formed,
2. no iron is deposited on the silica, but only onto the copper particles,
3. the iron is deposited below the surface of the copper particles.

EXAMPLE 4

A cylindrical stainless steel tube reactor (inner diameter 18 mm) was filled with 5.9 g of a Fe/Cu-SiO$_2$ catalyst which was prepared using the procedure described in Example 3. The iron content of the catalyst was about 2% by weight. The catalyst was activated by reduction in a flow of 10% H$_2$ and 90% N$_2$ at a temperature gradually increasing from 25° to 500° C. at a total pressure of 0.5 MPa.

Subsequently a reaction mixture comprising H$_2$, CO and N$_2$ (H$_2$:CO:N$_2$=2:1:3) was passed through the catalyst bed, which was kept at 500° C. The total pressure was 0.5 MPa at a space velocity of above 1200 h$^{-1}$. It was found that under these conditions 9.1×10$^{-7}$ mole ×sec$^{-1}$×g catalyst$^{-1}$ of carbon monoxide was converted to hydrocarbons. The product distribution of the hydrocarbons comprising alcohols obtained was approximately as follows:

| Component | Percentage per component of CO converted into hydrocarbons (%) |
|---|---|
| CH$_4$ | 61.9 |
| C$_2$H$_4$ | 2.8 |
| C$_2$H$_6$ | 20.3 |
| C$_2$H$_3$OH | 3.1 |
| C$_3$H$_6$ | 2.2 |
| C$_3$H$_8$ | 6.0 |
| C$_4$H$_{10}$ | 1.9 |
| other products | <2 |
| | ≈100% (9.1 × 10$^{-7}$ mole × sec$^{-1}$ × g catalyst$^{-1}$) |

We claim:

1. A process for the production of a catalyst containing metallic copper, silver, gold, platinum or palladium, in finely divided form as basis metal and at least one metal of Group VIII of the Periodic System of Elements as active component on an inert, refractory support, characterised in that the catalyst containing the basis metal is heated to a temperature above 100° C. and one or more carbonyls of metals different from the basis metal and belonging to Group VIII of the Periodic System is/are allowed to act on the heated catalyst to alloy those metals into the basis metal.

2. A process as claimed in claim 1, characterised in that the temperature of the catalyst containing the basis metal is below 700° C.

3. A process as claimed in claim 1, characterised in that the basis metal is copper.

4. A process as claimed in claim 1, characterised in that the metal alloyed in is iron and/or nickel.

5. A process as claimed in claim 1, characterised in that the catalyst used as starting product contains from 5 to 50% by weight of basis metal, based on the total weight of the support and the basis metal.

6. A process as claimed in claim 1, characterised in that the gaseous carbonyls are present in admixture with non-oxidising gases, the content of the gaseous carbonyls in the gas mixture amounting to at least 0.1% by volume.

7. A process as claimed in claim 1, characterised in that the carbonyls are allowed to act on the catalyst used as starting product in a fluidised bed reactor in which the catalyst particles are present in fluidised form.

8. A process as claimed in claim 7, characterised in that the particle size of the basis catalyst is between 0.05 mm and 1.0 mm.

9. A process as claimed in claim 8, characterised in that the particle size of the catalyst particles shows a narrow deviation range.

10. A process as claimed in claim 6, characterised in that the catalyst is heated to a temperature above 200° C.

11. A process as claimed in claim 7, characterised in that hot, non-oxidising gases are introduced into the fluidised bed reactor for the purpose of heating the catalyst particles to the desired temperature in a zone above the screen by which the fluidised bed is closed off underneath and which screen is kept at a temperature below 150° C.

12. A process as claimed in claim 1, characterised in that the catalyst containing the basis metal is thoroughly mixed with one or more powder-form metals different from the basis metal and belonging to Group VIII of the Periodic System of Elements and carbon monoxide is allowed to act on the resulting mixture in a reactor so that carbonyls are formed in situ.

13. A process as claimed in claim 12, characterised in that more than 90% by weight of the metal powder consists of monocrystalline metal particles without any crystal boundaries.

14. A process as claimed in claim 12, characterised in that the mixture is kept at a temperature of 100° to 250° C. for 10 minutes to 2 hours and then at a temperature at least 100° C. higher for 10 minutes to 2 hours, subsequently cooled by at least 100° C. and this heating/cooling cycle is repeated either once or several times.

15. Process of claim 6 wherein the content of the gaseous carbonyls in the gas mixture amounts to between 0.5 and 1.5% by volume.

16. Process of claim 6 wherein the content of the gaseous carbonyls amounts to between 0.6 and 1.1% by volume.

17. Process of claim 9 wherein the narrow deviation range is ±20% from that particle size which is common to most of the particles.

18. Process of claim 10 wherein the catalyst is heated to a temperature above 300° C.

19. A process as claimed in claim 6, wherein said non-oxidizing gases is nitrogen.

* * * * *